(12) United States Patent
Lamichhane et al.

(10) Patent No.: US 11,896,584 B2
(45) Date of Patent: *Feb. 13, 2024

(54) **OXAZOLIDINONE FOR TREATMENT OF INFECTIONS WITH *MYCOBACTERIUM TUBERCULOSIS***

(71) Applicants: The Johns Hopkins University, Baltimore, MD (US); University of St. Thomas, St. Paul, MN (US)

(72) Inventors: Gyanu Lamichhane, Towson, MD (US); J. Thomas Ippoliti, St. Paul, MN (US)

(73) Assignees: THE JOHNS HOPKINS UNIVERSTY, Baltimore, MD (US); UNIVERSITY OF ST. THOMAS, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/060,823

(22) Filed: Dec. 1, 2022

(65) Prior Publication Data

US 2023/0099803 A1 Mar. 30, 2023

Related U.S. Application Data

(63) Continuation of application No. 17/326,166, filed on May 20, 2021, now Pat. No. 11,524,002, which is a continuation of application No. 15/999,253, filed as application No. PCT/US2017/018248 on Feb. 17, 2017, now Pat. No. 11,040,025.

(60) Provisional application No. 62/296,160, filed on Feb. 17, 2016.

(51) Int. Cl.
*A61K 31/4245* (2006.01)

(52) U.S. Cl.
CPC .................. *A61K 31/4245* (2013.01)

(58) Field of Classification Search
CPC .................................................. A61K 31/4245
See application file for complete search history.

(56) References Cited

U.S. PATENT DOCUMENTS

| | | | |
|---|---|---|---|
| 5,399,363 A | 3/1995 | Liversidge et al. |
| 5,466,468 A | 11/1995 | Schneider et al. |
| 5,543,158 A | 8/1996 | Gref et al. |
| 5,580,579 A | 12/1996 | Ruddy et al. |
| 5,629,001 A | 5/1997 | Michael et al. |
| 5,641,515 A | 6/1997 | Ramtoola |
| 5,725,871 A | 3/1998 | Illum |
| 5,756,353 A | 5/1998 | Debs |
| 5,780,045 A | 7/1998 | McQuinn et al. |
| 5,792,451 A | 8/1998 | Sarubbi et al. |
| 5,804,212 A | 9/1998 | Illum |
| 6,559,305 B1 | 5/2003 | Bergren |
| 6,613,308 B2 | 9/2003 | Bartus et al. |
| 6,737,514 B1 | 5/2004 | Wang et al. |

FOREIGN PATENT DOCUMENTS

CN 104725330 6/2015

OTHER PUBLICATIONS

Boucher et al., Bad bugs, no drugs: no ESKAPE! An update from the Infectious Diseases Society of America. Clin Infect Dis. Jan. 1, 2009;48(1):1-12.
Cole et al., Deciphering the biology of Mycobacterium tuberculosis from the complete genome sequence. Nature. Jun. 11, 1998;393(6685):537-44.
Desmond, E. Clinical Laboratory Standard Institute 2011, M24-A2.
Dheda et al., Global control of tuberculosis: from extensively drug-resistant to untreatable tuberculosis. Lancet Respir Med. Apr. 2014;2(4):321-38.
Ebner et al., Synthesis of novel oxazolidinone antimicrobial agents. Bioorg Med Chem. Mar. 1, 2008;16(5):2651-6.
Fortun et al., Linezolid for the treatment of multidrug-resistant tuberculosis. J Antimicrob Chemother. Jul. 2005;56(1):180-5.
Hsieh et al., Synergy assessed by checkerboard. A critical analysis. Diagn Microbiol Infect Dis. May-Jun. 1993;16(4):343-9.
International Search Report and Written Opinion for PCT/US2017/018248, dated Aug. 24, 2017. 7 pages.
Kloss et al., Resistance mutations in 23 S rRNA identify the site of action of the protein synthesis inhibitor linezolid in the ribosomal peptidyl transferase center. J Mol Biol. Nov. 19, 1999;294(1):93-101.
Mathiowitz et al., Biologically erodable microspheres as potential oral drug delivery systems. Nature. Mar. 27, 1997;386(6623):410-4.
Rodriguez et al., In vitro activity of moxifloxacin, levofloxacin, gatifloxacin and linezolid against Mycobacterium tuberculosis. Int J Antimicrob Agents. Dec. 2002;20(6):464-7.
Saager et al., Molecular characterisation of linezolid resistance in two vancomycin-resistant (VanB) Enterococcus faecium isolates using Pyrosequencing. Eur J Clin Microbiol Infect Dis. Sep. 2008;27(9):873-8.

(Continued)

*Primary Examiner* — Kamal A Saeed
(74) *Attorney, Agent, or Firm* — Casimir Jones, SC; Jeffrey W. Childers

(57) ABSTRACT

The present invention is a method of treating or preventing *Mycobacterium tuberculosis* infection in a subject by administering to the subject an effective amount of oxazolidinone, specifically (N—(((S)-3-(dibenzo[b,e][1,4]dioxin-7-yl)-2-oxooxazolidin-5-yl)methyl)acetamide) or a pharmaceutically acceptable salt, solvate, or stereoisomer thereof.

4 Claims, No Drawings

(56) References Cited

OTHER PUBLICATIONS

Schumacher et al., Intracellular accumulation of linezolid in *Escherichia coli*, Citrobacter freundii and Enterobacter aerogenes: role of enhanced efflux pump activity and inactivation. J Antimicrob Chemother. Jun. 2007;59(6):1261-4.
Shinabarger. Mechanism of action of the oxazolidinone antibacterial agents. Expert Opin Investig Drugs. Aug. 1999;8(8):1195-202.
Spellberg et al., The epidemic of antibiotic-resistant infections: a call to action for the medical community from the Infectious Diseases Society of America. Clin Infect Dis. Jan. 15, 2008;46(2):155-64.
Takenaga et al., Microparticle resins as a potential nasal drug delivery system for insulin. J Control Release. Mar. 2, 1998;52(1-2):81-7.
Zhao et al., Evaluation of the Efficacy of Novel Oxazolidinone Analogues against Nontuberculous Mycobacteria In Vitro. Jpn J Infect Dis. 2015;68(6):520-2.
Zurenko et al., In vitro activities of U-100592 and U-100766, novel oxazolidinone antibacterial agents. Antimicrob Agents Chemother. Apr. 1996;40(4):839-45.

OXAZOLIDINONE FOR TREATMENT OF INFECTIONS WITH *MYCOBACTERIUM TUBERCULOSIS*

REFERENCE TO RELATED APPLICATIONS

This application is a continuation of U.S. patent application Ser. No. 17/326,166, filed May 20, 2021, now allowed, which is a continuation of U.S. patent application Ser. No. 15/999,253, filed Aug. 17, 2018, now U.S. Pat. No. 11,040,025, which claims the benefit of U.S. Provisional Patent Application No. 62/296,160, filed on Feb. 17, 2016, each of which is hereby incorporated by reference for all purposes as if fully set forth herein.

STATEMENT OF GOVERNMENTAL INTEREST

This invention was made with government support under grant number OD008459, awarded by the National Institutes of Health. The government has certain rights in the invention.

BACKGROUND OF THE INVENTION

In 2008, the Infectious Diseases Society of America (IDSA) made one or more ominous declaration(s) based on the ongoing explosion of antibiotic-resistant infections that continues to plague global health care. Equally alarming is the decline in the research and development of new antibiotics to deal with this threat of antibiotic resistant organisms. In 2009, IDSA sounded another alarm by emphasizing their concern that the infrastructure for discovering and developing new antibacterials continues to stagnate, thereby risking the future pipeline of antibacterial drugs. Of major concern are the community and health care associated infections with bacterial pathogens *Enterococcus faecium, Staphylococcus aureus, Klebsiella pneumoniae, Acinetobacter baumannii, Pseudomonas aeruginosa*, and *Enterobacter* species (or commonly abbreviated as ESKAPE) that are increasingly becoming resistant to drugs available to treat them.

The synthesis of a novel oxazolidinone, T145 (N—(((S)-3-(dibenzo[b,e][1,4]dioxin-7-yl)-2-oxooxazolidin-5-yl)methyl)acetamide) that exhibits antimicrobial potency against methicillin-sensitive *Staphylococcus aureus* was described (J.T. Bioorganic & Medicinal Chemistry 2008, 16, 2651). Linezolid, an oxazodilinone, initially labeled as U-100766, is a Food and Drug Administration approved antibacterial that is used for treatment of a wide range of bacterial pathogens. Oxazolidinones have a common 2-oxazolidone ring and inhibit initiation of protein synthesis by preventing formation of ribosome and N-formylmethionyl-tRNA complex. Resistance to oxazolidinones generally result from mutation in 23S rRNA, which supports its mechanism of action, or due to activity of efflux pumps.

Although the World Health Organization declared tuberculosis a global health threat more than 20 years ago, this year it increased its estimate of death from this disease to 1.5 million making it the number one bacterial infectious disease in the world. Although tuberculosis is an ancient disease and *Mycobacterium tuberculosis*, its etiological agent, was discovered in 1882, it continues to be a major global infectious disease. Emergence of multiple- and extensively-drug resistant strains of *Mycobacterium tuberculosis* in many regions of the world clearly demonstrates that efforts to innovate new agents against this pathogen have been inadequate.

SUMMARY OF THE INVENTION

One embodiment of the present invention is a method of treating or preventing *Mycobacterium tuberculosis* infection in a subject, an animal preferably a human, by administering to the subject an effective amount of a pharmaceutical composition comprising:

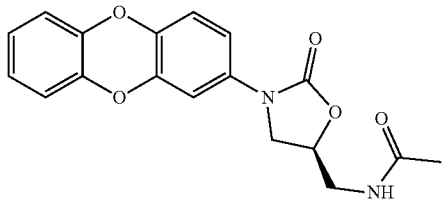 [SMILES: CC(=O)NC[C@H]1CN(c2ccc3c(c2)Oc2ccccc2O3)C(=O)O1]

T145: (N—(((S)-3-(dibenzo[b,e][1,4]dioxin-7-yl)-2-oxooxazolidin-5-yl)methyl)acetamide)

or a pharmaceutically acceptable salt, solvate, or stereoisomer thereof. Additionally one or more antimicrobial compounds may be administered.

Another embodiment of the present invention is a method for the selection and isolation of bacteria not sensitive to (N—(((S)-3-(dibenzo[b,e][1,4]dioxin-7-yl)-2-oxooxazolidin-5-yl)methyl)acetamide), preferably a Gram negative bacteria or *Mycobacterium abscessus*, comprising: providing a sample comprising a bacteria not sensitive to (N—(((S)-3-(dibenzo[b,e][1,4]dioxin-7-yl)-2-oxooxazolidin-5-yl)methyl)acetamide) and *Mycobacterium tuberculosis* or a Gram positive bacteria that is sensitive to (N—(((S)-3-(dibenzo[b,e][1,4]dioxin-7-yl)-2-oxooxazolidin-5-yl)methyl)acetamide); and applying an effective amount of (N—(((S)-3-(dibenzo[b,e][1,4]dioxin-7-yl)-2-oxooxazolidin-5-yl)methyl)acetamide) to the sample to inhibit the growth of the *Mycobacterium tuberculosis* or the Gram positive bacteria. The term "sensitive" means a bacteria having a minimum inhibitory concentration of 30 or less, preferably 20 or less, preferably 10 or less, and most preferably 5 or less, when treated with (N—(((S)-3-(dibenzo[b,e][1,4]dioxin-7-yl)-2-oxooxazolidin-5-yl)methyl)acetamide) is *Mycobacterium abscessus*. The term "not sensitive" means a bacteria having a minimum inhibitory concentration of greater than 5, preferably 10, preferably greater than 20, and most preferably greater than 30.

DETAILED DESCRIPTION OF THE INVENTION

T145 Inhibits Growth of *Enterococcus faecalis, Staphylococcus Aureus* and *Mycobacterium tuberculosis*

The antimicrobial potency of T145 was assessed against gram negatives *Klebsiella pneumoniae, Acinetobacter baumannii, Pseudomonas aeruginosa* and *Enterobacter cloacae*, gram positives *Enterococcus faecalis*, and methicillin-sensitive and -resistant *Staphylococcus aureus*, and acid fast pathogens *Mycobacterium abscessus, Mycobacterium avium* and *Mycobacterium tuberculosis* by determining minimum inhibitory concentration (MIC) and minimum bactericidal concentration (MBC). Linezolid, an oxazolidinone that is clinically used for treatment of bacterial infections, was used as a control. Meropenem, one of the most potent antimicrobial available in clinic today, was also included as an additional control in this study.

T145 exhibited potent activity against growth of *Mycobacterium tuberculosis* and gram positive pathogens *Staphylococcus aureus* and *Enterococcus faecalis* (Table 1). Both methicillin-sensitive and -resistant strains of *Staphylococcus aureus* (strains ATCC 29213 and ATCC 43300) were equally sensitive to T145 with a $MIC_{90}$ of 0.5-1.0 µg/ml. T145 displayed no activity against the gram negative pathogens *Enterobacter cloacae*, *Klebsiella pneumoniae* and *Pseudomonas aeruginosa* and non-tuberculosis mycobacteria *Mycobacterium abscessus* and *Mycobacterium avium*. The discovery that *Mycobacterium tuberculosis* was sensitive to T145 was surprising since T145 was thought to be a promising antimicrobial agent in the fight against resistant Gram-positive bacterial infections but not Gram-negative bacteria such as *E. coli* or acid fast bacteria such as *Mycobacterium tuberculosis*. As shown in Table 1, at least one Gram negative bacteria, *Acinetobacter baumannii*, was sensitive to T145, demonstrating the determination of whether a bacteria will be sensitive to T145 based on its Gram negative or Gram positive phenotype is unpredictable. *Mycobacterium tuberculosis* is an acid fast bacteria and does not belong to either Gram negative or Gram positive groups. *Mycobacterium abscessus* and *Mycobacterium avium* were not sensitive to T145, but *Mycobacterium tuberculosis* was sensitive to T145, demonstrating the effect of T145 on bacteria, specifically *Mycobacterium* is unpredictable (Table 1).

Three axenic isolates of *Acinetobacter baumannii* were evaluated for their susceptibilities against T145. *Acinetobacter baumannii* 6M-1b is an environmental strain isolated from Monocacy River, Maryland; 19606 is an ATCC typed strain and ACBA is a recent clinical strain isolated from a patient at the Johns Hopkins Hospital, Baltimore, who had been treated with a range of antibiotics. The environmental strain 6M-1b displayed sensitivity to T145, linezolid and meropenem with a $MIC_{90}$ of 0.25-4.0 (Table 1). Next, strain ATCC 19606 was marginally susceptible to T145 only ($MIC_{90}$=32-64 µg/ml). With an $MIC_{90}$ of >64 µg/ml for T145, linezolid and meropenem, the patient isolate ACBA was most resistant among the three strains. The environmental strain of *Acinetobacter baumannii* likely was not exposed to oxazolidinones in nature and consequently was never under selective pressure of this agent. The patient isolate ACBA is likely to have the most exposure to drugs amongst the three strains. This data suggests that an increasing exposure to drugs has allowed *Acinetobacter baumannii* to develop considerable resistance to evolved oxazolidinones T145.

It is noteworthy that potency of T145 is several fold superior to meropenem against *Enterococcus faecalis* and *Mycobacterium tuberculosis*. The 0.5-1.0 µg/ml $MIC_{90}$ of T145 against *Mycobacterium tuberculosis* is comparable to 0.5-2.0 µg/ml $MIC_{90}$ of linezolid, a clinically used oxazolidinone. Today linezolid is one of the second line drugs used for treatment of multi- and extensively-resistant tuberculosis based on its in vivo potency to treat *Mycobacterium tuberculosis* infections. Clinical utility of T145 will be largely determined by its pharmacokinetic, pharmacodynamics and toxicity characteristics.

TABLE 1

Minimum inhibitory concentrations ($MIC_{90}$) of T145 and T197 in µg/ml. Data shown in this table were verified with two repeats of MIC determination. Meropenem and linezolid were used as - controls, ND = not done.

| Organism | $MIC_{90}$ (µg/ml) | | |
|---|---|---|---|
| | T145 | Linezolid | Meropenem |
| Gram negatives | | | |
| *Acinetobacter baumannii* 6M-1b | 0.25-0.50 | 0.25-0.50 | 1-2 |
| *Acinetobacter baumannii* ATCC 19606 | 32-64 | >64 | >64 |
| *Acinetobacter baumannii* ACBA | >64 | >64 | >64 |
| *Enterobacter cloacae* | >64 | >64 | 0.13-0.25 |
| *Klebsiella pneumoniae* | >64 | 16-32 | <0.06 |
| *Pseudomonas aeruginosa* | >64 | >64 | 0.25-0.50 |
| Gram positives | | | |
| *Staphylococcus aureus* methicillin-sensitive | 0.5-1.0 | 1-2 | 0.06-0.13 |
| *Enterococcus faecalis* | 0.25-0.50 | 1-2 | 4-8 |
| Mycobacteria | | | |
| *Mycobacterium tuberculosis* | 0.5-1.0 | 0.2-2.0[4,11] | 4-8 |
| *Mycobacterium abscessus* | >64 | ND | >64 |
| *Mycobacterium avium* | >64 | ND | >64 |

T145 is Bactericidal Against *Mycobacterium tuberculosis* but Bacteriostatic Against *Enterococcus faecalis* and *Staphylococcus aureus*

To investigate the antimicrobial mechanism of T145 the inventors determined minimum bactericidal concentration ($MBC_{99.9}$), the concentration of drug at which 99.9% of bacilli are killed, for *Mycobacterium tuberculosis*, *Enterococcus faecalis* and *Staphylococcus aureus*. For this, each pathogen was incubated in the presence of T145 at 1, 2, 4 and 8 times respective $MIC_{90}$ and the number of surviving bacilli were enumerated from observed colony forming units. T145 exhibited bactericidal activity against *Mycobacterium tuberculosis* with $MBC_{99.9}$ of 2 µg/ml. *Enterococcus faecalis* and *Staphylococcus aureus* grew confluently on solid medium containing up to 8 times the $MIC_{90}$ of T145. Based on the lack of observable difference in CFU at and up to 8 times $MIC_{90}$, the conclusion was that T145 is bacteriostatic against *Enterococcus faecalis* and *Staphylococcus aureus*. Linezolid also exhibits bacteriostatic activity against *Staphylococcus aureus*.

Frequency of Spontaneous Mutation Conferring Resistance

As a therapeutic agent, a drug becomes useless for treatment of infections with strains that develop resistance for it. Therefore, the frequency at which spontaneous genetic mutation(s) that render a pathogen resistant to a drug arise is a measure of the longevity of the drug. *Mycobacterium tuberculosis*, *Enterococcus faecalis* and *Staphylococcus aureus* were subjected to T145 at 5×-60×$MIC_{90}$ to determine the frequency of spontaneous resistant mutants. The inventors were able to isolate *Mycobacterium tuberculosis* mutants after 5 weeks of incubation at 5× and 10×$MIC_{90}$ of T145 and conclude that spontaneous mutants that confer resistance to T145 arise at a frequency of $4.0 \times 10^{-8}$. *Enterococcus faecalis* and *Staphylococcus aureus* did not form classical distinct single colonies on agar plates containing T145. The inventors consistently observed a thin semi-transparent layer atop agar, which we determined was the initial 1 ml culture deposited on it, on every plate that contained T145 at concentrations up to 60×$MIC_{90}$. Repeat attempts to select spontaneous mutants failed to produce distinct colonies. We hypothesize that T145 is bacteriostatic against Enterococcus faecalis and Staphylococcus aureus up to 60× respective $MIC_{90}$ and prevents selection of spontaneous resistant mutants. To test this hypothesis, we scraped the dried semi-transparent layer and transferred to fresh medium. The recovered organisms grew consistently in liquid broth lacking T145 but failed to grow in its presence at its $MIC_{90}$.

Antimicrobial Activity of T145 in Combination with Carbapenems

Carbapenems are a sub-class of β-lactams and derive their antimicrobial potency by inhibiting peptidoglycan biosynthesis. The inventors hypothesized that inhibition of two essential pathways, namely protein synthesis by oxazolidinone T145 and peptidoglycan biosynthesis by carbapenems, may result in synergistic killing of bacterial pathogens. To evaluate if synergy (or indifference or antagonism) in antimicrobial activity exists between T145 and carbapenems, the inventors used a checkboard titration assay and subjected Enterococcus faecalis and methicillin-sensitive and -resistant strains of Staphylococcus aureus to combination of the two agents, each at defined concentrations ranging from $1 \times MIC_{90}$ to $\frac{1}{16} \times MIC_{90}$.

Parenterally administered carbapenems doripenem and biapenem, an orally bioavailable penem faropenem and carbapenem tebipenem were studied as representatives of this class of β-lactams. Both Enterococcus faecalis and Staphylococcus aureus are sensitive to these drugs (Table 2). Growth inhibition of pathogens tested was not observed in any wells containing less than ½ $MIC_{90}$ of T145 or carbapenems demonstrating that antibacterial activity of T145 does not synergize with the tested carbapenems. Growth of the organisms was inhibited in wells containing T145 at ≥½ $MIC_{90}$. Based on these data the inventors conclude that antimicrobial activity of T145 is indifferent (neither antagonistic nor synergistic) when combined with doripenem, biapenem, faropenem and tebipenem.

The inventors also evaluated if any drug-drug interaction existed between T145 and isoniazid or rifampicin, two drugs that comprise the backbone of tuberculosis treatment today, against Mycobacterium tuberculosis using the checkerboard assay as described above. Any antagonism or synergy between T145 and isoniazid or rifampicin is not observed, and therefore that activity of T145 against Mycobacterium tuberculosis is indifferent to that of isoniazid or rifampicin.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

TABLE 2

In vitro activity of doripenem, biapenem, faropenem and tebipenem against Enterococcus faecalis, methicillin-sensitive Staphylococcus aureus and Mycobacterium tuberculosis. Minimum inhibitory concentrations ($MIC_{90}$) in µg/ml are reported here.

| | $MIC_{90}$ (µg/ml) | | |
|---|---|---|---|
| | Enterococcus faecalis | Staphylococcus aureus | Mycobacterium tuberculosis |
| Doripenem | 0.25-0.50 | 0.003-0.007 | 2.5-5.0 [15] |
| Biapenem | 0.25-0.50 | 0.007-0.015 | 2.5-5.0 [15] |
| Faropenem | 0.25-0.50 | 0.015-0.03 | 2.5-5.0 [15] |
| Tebipenem | 0.25-0.50 | 0.03-0.06 | 1.25-2.5 [15] |

EXAMPLES/METHODS

Bacterial Strains and In Vitro Growth Conditions

Mycobacterium tuberculosis H37Rv, Mycobacterium abscessus ATCC 19977, Mycobacterium avium 104 (isolated from an adult AIDS patient in Southern California in 1983), Acinetobacter baumannii 6M-1 b (an isolate from Monocacy River, Frederick, Maryland), Acinetobacter baumannii ATCC 19606, Acinetobacter baumannii ACBA (isolated from patient at the Johns Hopkins Hospital) Enterococcus faecalis ATCC 19433, methicillin-sensitive Staphylococcus aureus ATCC 29213, Enterobacter cloacae ATCC 13047, Klebsiella pneumoniae ATCC 35657 and Pseudomonas aeruginosa PA14 were used. Mycobacterium tuberculosis, M. avium and M. abscessus were grown in Middlebrook 7H9 broth (Difco), containing 0.5% glycerol, 10% oleic acid-albumin-dextrose-catalase (OADC) and 0.05% Tween 80 or on Middlebrook 7H110 agar plates at 37° C. Acinetobacter baumannii, Enterococcus faecalis, Staphylococcus aureus, Enterobacter cloacae, Klebsiella pneumoniae and Pseudomonas aeruginosa were grown in cation-adjusted Mueller-Hinton broth (Becton-Dickinson). Liquid cultures were grown with constant shaking at 220 round per minute at 37° C. Meropenem, doripenem, faropenem, biapenem, tebipenem, clarithromycin and isoniazid were commercially acquired (Sigma-Aldrich). T145 was synthesized in the laboratory to a purity of greater than 99%.

Minimum Inhibitory Concentration

Minimum inhibitory concentration ($MIC_{90}$) for Mycobacterium tuberculosis was determined using standard broth macrodilution in 15-ml sterile conical tubes containing 2.5 ml of 7H9 broth. Standard broth microdilution method (using 96-well plates) was used for other organisms as per Clinical and Laboratory Standard Institute recommendations. Middlebrook 7H9 broth was used for *Mycobacterium abscessus, Mycobacterium avium* and *Mycobacterium tuberculosis* and cation-adjusted Mueller-Hinton broth (Becton-Dickinson) was used for other organisms as per Clinical and Laboratory Standard Institute (CLSI) guidelines. In summary, $10^5$ bacilli grown to exponential phase in liquid medium were inoculated into each well containing drug at two fold dilutions ranging from 64 µg/ml to 0.03 µg/ml. Growth medium alone and without drug but inoculated with $10^5$ bacilli were included as negative and positive controls, respectively. Appropriate drugs (isoniazid for *Mycobacterium tuberculosis*, doripenem for *Mycobacterium abscessus*, clarithromycin for *Mycobacterium avium* and meropenem for *Acinetobacter baumannii, Enterococcus faecalis, Staphylococcus aureus, Enterobacter cloacae, Klebsiella pneumoniae* and *Pseudomonas aeruginosa*) were included as positive control for growth inhibition. Growth was evaluated by visual inspection following incubation (at 35° C. for 18 hours for *Acinetobacter baumannii, Enterococcus faecalis*, methicillin-sensitive *Staphylococcus aureus, Enterobacter cloacae, Klebsiella pneumoniae* and *Pseudomonas aeruginosa*, fourteen days for *Mycobacterium tuberculosis* at 37° C., seven days at 37° C. for *M. avium* and at 30° C. for 3 days for *Mycobacterium abscessus*) as per CLSI guidelines.[18] $MIC_{90}$ is expressed as a range spanning two concentrations: the higher concentration represents the lowest concentration at which bacterial growth could not be observed.

Minimum Bactericidal Concentration

Minimum bactericidal concentration ($MBC_{99.9}$), the minimum concentration of drug that kills 99.9% of bacilli, was determined by extending the broth microdilution assay described above. Surviving bacilli or colony forming units (CFU) in well in which growth could not be observed were determined by growing them on agar plates containing appropriate growth medium and enumerating CFU (after 2 days of incubation at 37° C. for *Acinetobacter baumannii, Enterococcus faecalis, Staphylococcus aureus* and *Mycobacterium abscessus* and 21 days for *Mycobacterium tuberculosis*). The CFU at the initiation of the study, determined by enumerating live bacilli from initial inoculum on agar plates, is the input inoculum. The concentration of the agent at which 99.9% of the input CFU is killed is reported here as $MBC_{99.9}$.

Checkerboard Titration Assay

This assay is a modification of the broth dilution assay and was carried out as described. In summary, each well containing $10^5$ CFU received two drugs each in two fold dilutions below their respective $MIC_{90}$. The suspensions are incubated at 37° C. and growth was evaluated as described above. Fractional Inhibitory Concentration (FIC) of a drug in a combination that inhibits bacterial growth is the concentration of the drug in the well divided by $MIC_{90}$ of the drug if used alone. The sum of FIC of each drug in the combination is the FIC index. In each well where bacterial growth was absent, FIC index was calculated and an average FIC index was determined. Drug-drug antagonism was inferred if average FIC index is >2, indifference if 0.5-2.0 and synergy if ≤0.5.

Determination of Frequency of Drug Resistance Emergence

Each organism was grown as described above to exponential phase, a suspension with optical density ($A_{600\ nm}$) of 1.0 was prepared and 1.0 ml of this suspension was spread onto each plate containing solid agar with growth media that was supplemented with T145 at 4-20× respective $MIC_{90}$. Five plates were used for each concentration of T145 studied. Colonies that grew at 37° C. (>2-3 days of incubation for *Staphylococcus aureus* and 21 days for *Mycobacterium tuberculosis*) were enumerated as spontaneous mutants resistant to T145. Colonies that grew on medium lacking T145 were enumerated as input CFU. The number of resistant mutants as a percentage of the input CFU inoculum was calculated as the frequency of spontaneous mutants resistant to T145.

Embodiments of the disclosure concern methods and/or compositions for treating and/or preventing a bacterial infection, such as *Mycobacterium tuberculosis*, in a subject. In certain embodiments, individuals with a bacterial infection such as *Mycobacterium tuberculosis* are treated with a chemical entity of the present invention, such as T145.

In certain embodiments, the level to which one or more chemical entities of the present invention inhibits the grow of a bacteria may be any level so long as it provides amelioration of at least one symptom of the bacterial infection. The level of bacterial growth may decrease by at least 2, 3, 4, 5, 10, 25, 50, 100, 1000, or more fold expression compared to the level of expression in a standard, or when compared to person who has a bacteria infection but is not administered a chemical entity of the present invention, at least in some cases. An individual may monitor the growth of bacteria using standard methods in the art. An individual known to have a bacterial infection or suspected of having a bacterial infection may be provided an effective amount of chemical entity of the present invention, including T145.

In particular embodiments of the disclosure, an individual is given an antibacterial agent in addition to the one or more chemical entities of the present invention. When combination therapy is employed with one or more chemical entities of the present invention, the additional therapy may be given prior to, at the same time as, and/or subsequent to the chemical entity of the present invention such as T145.

Pharmaceutical Preparations

Pharmaceutical compositions of the present invention comprise an effective amount of one or more chemical entities of the present invention such as T145, dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that comprises at least one chemical entity of the present invention, or additional active ingredient, will be known to those of skill in the art in light of the present disclosure, as exemplified by Remington: The Science and Practice of Pharmacy, 21$^{st}$ Ed. Lippincott Williams and Wilkins, 2005, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

A pharmaceutical composition including a chemical entity of the present invention may comprise different types of carriers depending on whether it is to be administered in solid, liquid or aerosol form, and whether it need to be sterile for such routes of administration as injection. The present compositions, can be administered intravenously, intradermally, transdermally, intrathecally, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like. Further in accordance with the present disclosure, the composition of the present invention suitable for administration is provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of a composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof. In accordance with the present invention, the composition is combined with the carrier in any convenient and practical manner, i.e., by solution, suspension, emulsification, admixture, encapsulation, absorption and the like. Such procedures are routine for those skilled in the art.

In a specific embodiment of the present invention, the composition is combined or mixed thoroughly with a semi-solid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in an the composition include buffers, amino acids such as glycine and lysine, carbohydrates such as dextrose, mannose, galactose, fructose, lactose, sucrose, maltose, sorbitol, mannitol, etc.

In further embodiments, the present invention may concern the use of a pharmaceutical lipid vehicle compositions that include a chemical entity of the present invention, one or more lipids, and an aqueous solvent. As used herein, the term "lipid" will be defined to include any of a broad range of substances that is characteristically insoluble in water and extractable with an organic solvent. This broad class of compounds are well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of the present invention.

One of ordinary skill in the art would be familiar with the range of techniques that can be employed for dispersing a composition in a lipid vehicle. For example, the antibacterial chemical entities of the present inventions (or compositions) may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

Alimentary Compositions and Formulations

In one embodiment of the present disclosure, the antibacterial chemical entities of the present invention are formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain embodiments, the active compounds may be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. Nos. 5,641,515; 5,580,579 and 5,792, 451, each specifically incorporated herein by reference in its entirety). The tablets, troches, pills, capsules and the like may also contain the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings prevent denaturation of the composition in the stomach or upper bowel where the pH is acidic. See, e.g., U.S. Pat. No. 5,629,001. Upon reaching the small intestines, the basic pH therein dissolves the coating and permits the composition to be released and absorbed by specialized cells, e.g., epithelial enterocytes and Peyer's patch M cells. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

For oral administration the compositions of the present disclosure may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

Additional formulations which are suitable for other modes of alimentary administration include suppositories. Suppositories are solid dosage forms of various weights and shapes, usually medicated, for insertion into the rectum. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

Parenteral Compositions and Formulations

In further embodiments, one or more chemical entities of the present invention may be administered via a parenteral route. As used herein, the term "parenteral" includes routes that bypass the alimentary tract. Specifically, the pharmaceutical compositions disclosed herein may be administered for example, but not limited to intravenously, intradermally, intramuscularly, intraarterially, intrathecally, subcutaneous, or intraperitoneally U.S. Pat. Nos. 67,537,514, 6,613,308, 5,466,468, 5,543,158; 5,641,515; and 5,399,363 (each specifically incorporated herein by reference in its entirety).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in isotonic NaCl solution and either added hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

Miscellaneous Pharmaceutical Compositions and Formulations

In other preferred embodiments of the invention, the active antibacterial compound of the present invention, such as T145, may be formulated for administration via various miscellaneous routes, for example, topical (i.e., transdermal) administration, mucosal administration (intranasal, vaginal, etc.) and/or inhalation. Pharmaceutical compositions for topical administration may include the active compound formulated for a medicated application such as an ointment, paste, cream or powder. Ointments include all oleaginous, adsorption, emulsion and water-solubly based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the active ingredient and provide for a homogenous mixture. Transdermal administration of the present invention may also comprise the use of a "patch". For example, the patch may supply one or more active substances at a predetermined rate and in a continuous manner over a fixed period of time.

In certain embodiments, the pharmaceutical compositions may be delivered by eye drops, intranasal sprays, inhalation, and/or other aerosol delivery vehicles. Methods for delivering compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

The term aerosol refers to a colloidal system of finely divided solid of liquid particles dispersed in a liquefied or pressurized gas propellant. The typical aerosol of the present invention for inhalation will consist of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

Kits of the Disclosure

Any of the compositions and/or chemical entities described herein may be comprised in a kit. In a non-limiting example, an antibacterial chemical entity of the present invention (for example, T145) may be comprised in a kit.

The kits may comprise a suitably aliquoted inducer of antibacterial chemical entities of the present invention and, in some cases, one or more additional agents. The component(s) of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present invention also will typically include a means for containing the one or more chemical entities of the present invention and any other reagent containers in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being particularly preferred. The composition(s) of the present invention may be formulated into a syringeable composition. In which case, the container means may itself be a syringe, pipette, and/or other such like apparatus, from which the formulation may be applied to an infected area of the body, injected into an animal, and/or even applied to and/or mixed with the other components of the kit. However, the components of the kit may be provided as dried powder(s). When reagents and/or components are provided as a dry powder, the powder can be reconstituted by the addition of a suitable solvent. It is envisioned that the solvent may also be provided in another container means.

The invention claimed is:

1. A method for treating or preventing a methicillin-sensitive and/or methicillin-resistant *Staphylococcus aureus* infection in a subject in need thereof, the method comprising administering to the subject an effective amount of (N—(((S)-3-(dibezo[b,e][1,4]dioxin-7-yl)-2-oxooxazolidin-5-yl)methyl)acetamide) or a pharmaceutically acceptable salt, solvate, or stereoisomer thereof.

2. The method of claim 1 wherein the subject is a human.

3. The method of claim 1 wherein the subject is an animal.

4. The method of claim 1 further administering at least one or more antimicrobial compounds.

* * * * *